United States Patent [19]
Lue et al.

[11] Patent Number: 4,585,005
[45] Date of Patent: Apr. 29, 1986

[54] METHOD AND PACEMAKER FOR STIMULATING PENILE ERECTION

[75] Inventors: Tom P. Lue, Millbrae; Emil A. Tanagho, San Rafael; Richard A. Schmidt, San Francisco, all of Calif.

[73] Assignee: Regents of University of California, Berkeley, Calif.

[21] Appl. No.: 597,502

[22] Filed: Apr. 6, 1984

[51] Int. Cl.⁴ .............................................. A61N 1/32
[52] U.S. Cl. .................. 128/419 R; 128/794
[58] Field of Search ............ 128/419 E, 419 R, 419 S, 128/421, 422, 423 R, 794

[56] References Cited

U.S. PATENT DOCUMENTS

| | | | |
|---|---|---|---|
| 3,403,684 | 10/1968 | Stiebel et al. | 128/407 |
| 3,646,940 | 3/1972 | Timm et al. | 128/421 |
| 3,650,276 | 3/1972 | Burghele et al. | 128/419 E |
| 3,662,758 | 5/1972 | Glover | 128/419 E |
| 3,667,477 | 6/1972 | Susset et al. | 128/419 E |
| 3,727,616 | 4/1973 | Lenzkes | 128/422 |
| 3,870,051 | 3/1975 | Brindley | 128/422 |
| 3,941,136 | 3/1976 | Bucalo | 128/422 |
| 4,102,344 | 7/1978 | Conway et al. | 128/419 |
| 4,106,511 | 8/1978 | Elandsson | 128/407 |
| 4,237,899 | 12/1980 | Hagfors et al. | 128/422 |
| 4,279,256 | 7/1981 | Bucalo | 128/419 R |
| 4,387,719 | 6/1983 | Plevalk et al. | 128/421 |
| 4,400,590 | 8/1983 | Michelson | 179/107 FD |
| 4,406,288 | 9/1983 | Horwinski et al. | 128/422 |

FOREIGN PATENT DOCUMENTS

516707 1/1931 Fed. Rep. of Germany ...... 128/794

OTHER PUBLICATIONS

Richard et al., "Vetrinary Medicine/Small Animal Clinician" Aug., 1974, pp. 1029–1031.

Primary Examiner—William E. Kamm
Attorney, Agent, or Firm—Phillips, Moore, Lempio & Finley

[57] ABSTRACT

The problem of providing a method and device for stimulating penile erection for a sexually disabled patient includes the implantation of an electrode on the cavernous nerves of a human male, adjacent to his prostate gland. Each electrode is electrically connected to a receiver, subcutaneously implanted on the patient. An external transmitter is utilized to electrically energize the receiver to transmit electrical energy to the electrode and the cavernous nerves for penile erection purposes.

9 Claims, 4 Drawing Figures

FIGURE 2
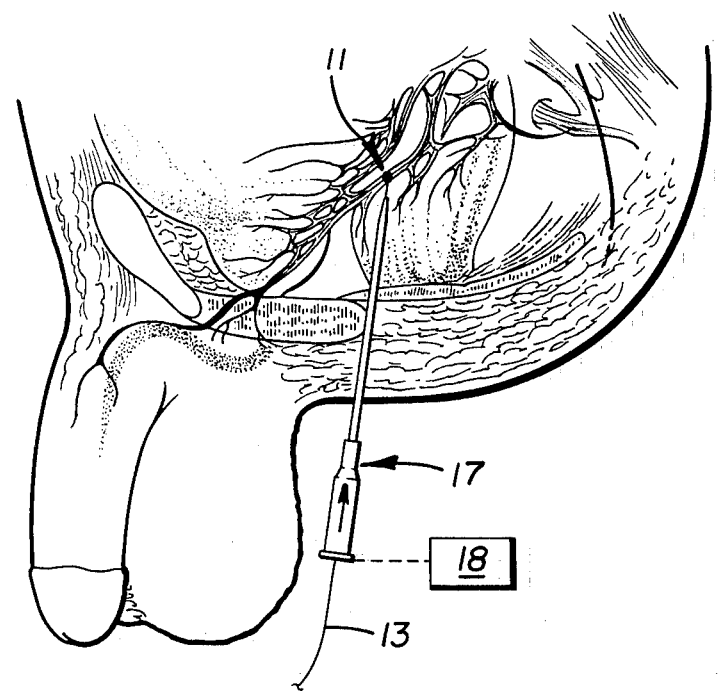
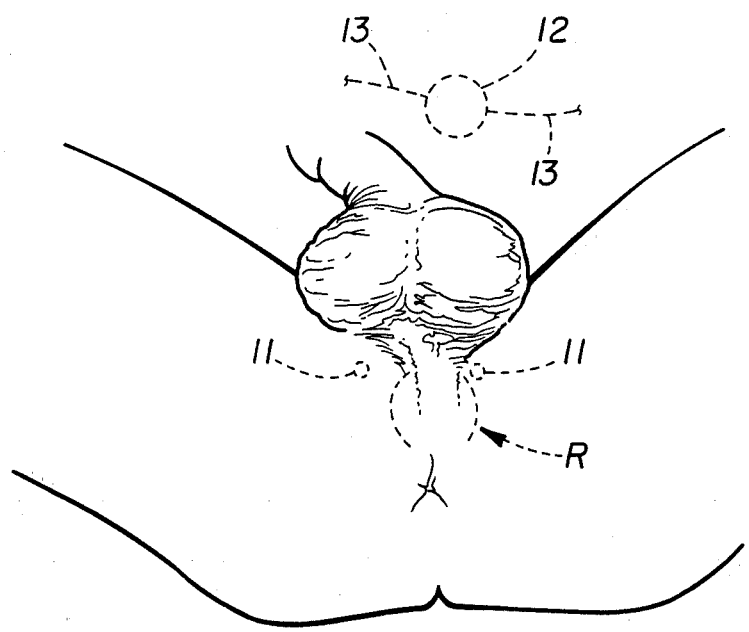
FIGURE 3

METHOD AND PACEMAKER FOR STIMULATING PENILE ERECTION

DESCRIPTION

1. Technical Field

This invention relates generally to a method and device for stimulating penile erection and more particularly to an implantable erection stimulator for providing controlled and sustained penile erection for patients who are incapable of obtaining such erection spontaneously.

2. Background Art

The need for a method to provide a controlled and sustained penile erection in a male patient who is incapable of obtaining it spontaneously is well documented. Such impotency may be psychogenic, vasculogenic, hormonal or neurogenic. For example, a male patient may be suffering from a spinal injury or intractable psychogenic disturbance that renders him impotent.

Urologists, in particular, are intimately familiar with the high incidence of impotence after radical prostatectomy, radical cystectomy and abdominoperineal resection. In addition, impotence occurs occasionally after transurethral resection of a prostate, external sphincterotomy, internal urethrotomy and prostatic abscess. Mechanical, vascular, neurological and psychological etiologies have been suggested. Recently, the neuroanatomy of the pelvic plexus in the human fetus was reexplored and the neurologic origin of impotence after radical prostatectomy was stressed.

It is conventional practice to treat disabled patients of this type by the intrapenile insertion of a Silastic prosthesis, whether rigid, semi-rigid, or inflatable. One of the most common penile prosthetics is the so-called Scott inflatable type. Operations of this type tend to severly damage or destroy substantially all of the erectile tissues within the corpora cavernosa of the penis. As a result, the erection is unnatural and mechanical, i.e., non-physiologic.

The mechanism and hemodynamics of penile erection have long been a matter of controversy and assumption. During the nineteenth century, venous occlusion was thought to be the main factor in maintaining an erection, whereas more recent investigators have demonstrated increased blood flow as the cause of penile tumescence. On the basis of histologic study of various human cadaveric penises, it has been proposed to provide cushions or posters in the deep arteries of the penis and further provide arterial venous shunting as the controlling mechanism of erection. Further proposals suggest that erection occurs when rapid increases of arterial flow far exceed venous flow. In the latter studies, the venous flow rate was measured and found to be approximately seven times that found in association with the nonerect state of a penis.

During the past few years, erection studies were conducted on human volunteers who received injections of xenon and radiopaque contrast material into the corpus cavernosum, whereafter the volunteers were subjected to visual erotic stimulation. In one study, it was concluded that during erection venous flow from the corpora was increased and tumescence was created by a markedly increased arterial flow far exceeding the venous flow. In another and contra study, a descreased xenon clearance and decreased egress of contrast material from the corpora cavernosa were found. However, a rapid venous outflow was demonstrated at the early phase of detumescence. These contradictory reports further added to the confusion in the understanding of the mechanism of erection.

Although the "nervi erigentes" were recognized in the mid-nineteenth century, the detailed neuroanatomy of penile erection has not been made clear. Most of the available information was derived from ablation studies done after either neurosurgical procedure or neurological injury. Erection was arbitrarily divided into psychogenic or reflexogenic. Psychogenic erection was said to result from tactile, auditory, olfactory or visual stimuli to the cerebral cortex and to be mediated through the sympathetic (thoracolumbar) pathway.

Reflexogenic erection from direct genital stimulation was said to have its afferent limb in the pudendal nerve and efferent limb through pelvic parasympathetic nerves. Both of these efferent nerve tracts for erection were described to be located near the pyramidal tracts and just lateral to the central canal (Fasciculus epididymalis) of the spinal cord. The sacral spinal segments responsible for erection were also suggested as a result of certain studies.

The nervi erigentes were studied in the human fetus, but their detailed anatomy in the adult male has not been well defined. The exact location and organization of the spinal nuclei responsible for erection were also unknown. This lack of information is probably the major factor contributing to the increased number of iatrogenic sexual cripples created by pelvic operations.

In summary, numerous studies have been made in respect to the motor nerves (nervi erigentes) and the mechanism and hemodynamics of penile erection. However, to applicants' knowledge, no suggestion has been made in the art to provide method and means for physiologically stimulating penile erection in a closely controlled and sustained manner. For example, U.S. Pat. No. 3,403,684 to A. I. Stiebel, et al. for "Electrical Stimulator" ostensibly teaches a device adapted to be inserted into the rectum, in the region of the prostate gland, to induce penile erection. U.S. Pat. No. 3,941,136 to L. Bucalo for "Method for Artificially Inducing Urination, Defecation, or Sexual Excitation" discloses the utilization of electrodes for ostensibly inducing a penile erection or other bodily functions. These prior art devices and methods involve either surface stimulation techniques or transrectal application and tend to be ineffectual for most applications under consideration herein.

DISCLOSURE OF INVENTION

This invention overcomes the above prior art problems by providing a method for stimulating penile erection in a closely controlled and sustained manner. The invention is particularly adapted for use by patients who are sexually disabled, such as those having spinal injuries or intractable psychogenic disturbances.

This invention enables the medical profession to provide such penile erection stimulus by first identifying the anatomical location of at least cavernous nerve of a penis, implanting an electrode at least closely adjacent to the cavernous nerve, implanting a subcutaneous receiver on the patient, and then electrically connecting the electrode to the receiver. Thus, an external transmitter can be utilized to selectively stimulate the cavernous nerve via the receiver and electrode.

In the preferred embodiment of this invention, an electrode is placed on each of the two cavernous nerves of a patient with each electrode being positioned on the portion of the respective cavernous nerve posterolateral to the prostatic capsule and between the apex of the capsule and the sacral nerves.

BRIEF DESCRIPTION OF THE DRAWINGS

Other advantages and objects of this invention will become apparent from the following description and accompanying drawings wherein:

FIG. 2 is a view generally similar to FIG. 1, but illustrates the percutaneous insertion of a spinal needle and implantation of a wire electrode therethrough;

FIG. 3 illustrates the positions of a pair of implanted electrodes adjacent to a prostate gland R.

BEST MODE OF CARRYING OUT THE INVENTION

Figure 1:
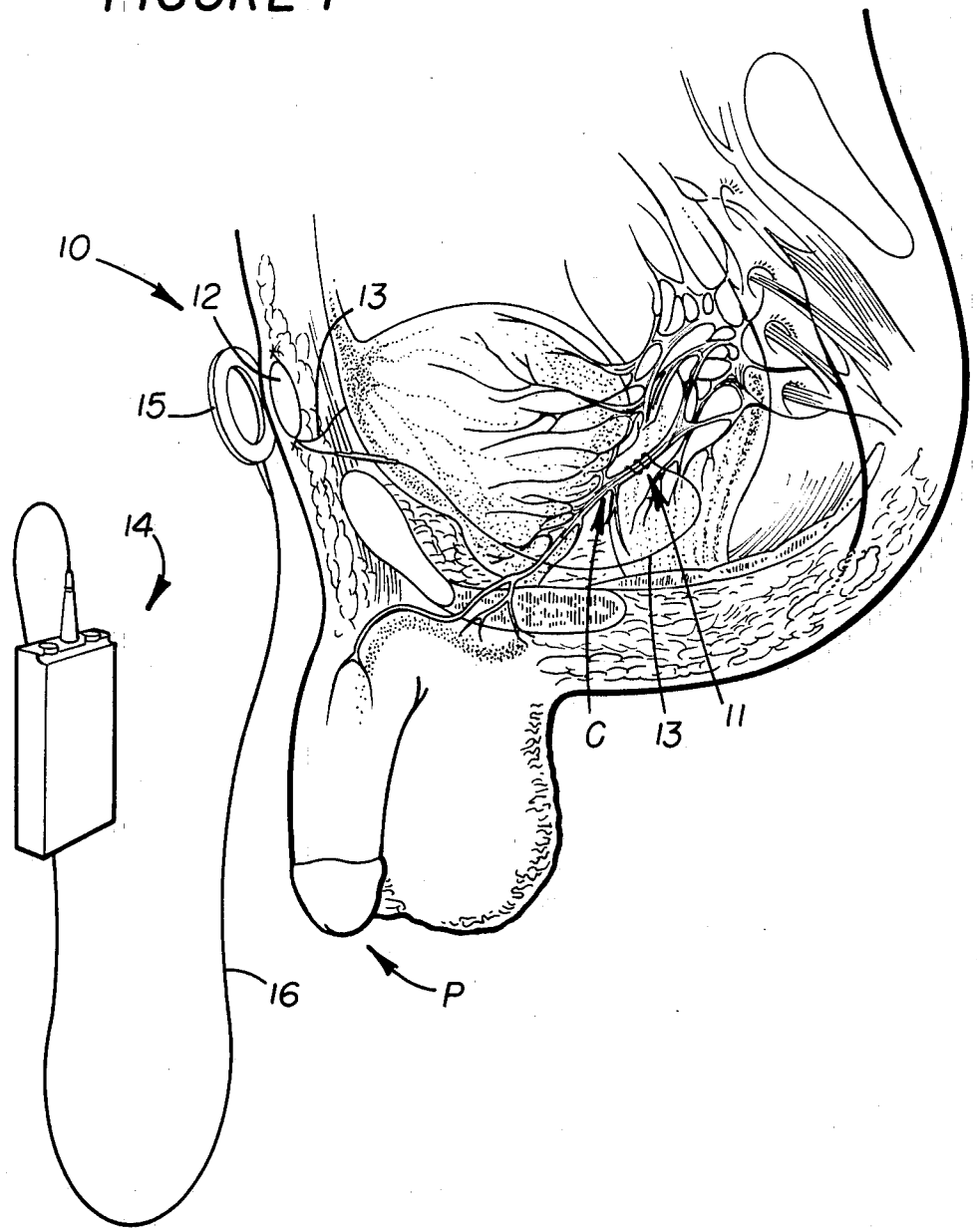
FIG. 1 is an anatomical view of the pelvic plexus region in a human male, illustrating the surgical implanation of an electrode and subcutaneous receiver of apparatus by an open operative approach to permit selective penile erection by use of an external transmitter.

FIG. 1 schematically illustrates various glands, nerves and related anatomical structures located in the pelvic plexus region of a human male. This invention is generally directed to a method and pacemaker system 10 for stimulating erection of a penis P, including the implantation of a pair of electrodes 11 (one shown) at critical anatomical locations in the illustrated patient. As discussed above, the method of this invention are particularly adapted for use for patients who are incapable of obtaining penile erections spontaneously due to sexual disablement, such as spinal injury, intractable psychogenic disturbances or the like.

As further discussed above, neither the neuroanatomy of erection in the adult male nor the associated mechanism and hemodynamics of such erection have been well defined heretofore. The inventors herein, through extensive exploratory surgery, experimentation, and study, have been successful in isolating such location and have further proved that by use of their method and pacemaker system, an otherwise sexually disabled male human can be rendered physiologically sexually potent.

The erection resulting from use of this invention, wherein tumescence of the glans and corpus spongiosum of the penis is evidenced, is natural and closer to the natural process than that effected by use of an intrapenile prosthesis. As further discussed above, the latter type of prosthesis, whether rigid, semi-rigid or inflatable, will normally cause destruction of substantially all of the erectile tissue within the corpora cavernosa of the penis. Further advantage of applicants' invention resides in the fact that erection is non-permanent and will not hinder possible transurethral procedures, as does the rigid or semi-rigid prosthesis. Furthermore, this invention will not damage the erectile tissue within the corpora cavernosa of the penis which may become important should the patient later recover from the underlying disease affecting his impotency and again desire to regain his ability to achieve a totally natural erection.

Experimentation Leading to Conception of Apparatus

As discussed above, the neural anatomy of erection in the adult male has not been well-defined previously. Firstly, the inventors herein systematically gained knowledge regarding the human nervi erigentes from the spinal center of a human male to his erectile tissue to isolate the pair of cavernous nerves C (one shown in FIG. 1), on or about which the electrode 11 is adapted to be implanted for the purpose of stimulating penile erection.

The anatomy and isolation of the nervi erigentes for acute and chronic neural stimulation for penile erection in dogs and monkeys proved successful and led to the investigation of the anatomy of such nerves in human males by cadaveric dissection and serial histologic sectioning. Experience in tracing spinal nuclei responsible for viscecal and urethral functions by transport of horseradish peroxidase (HRP) further enabled the inventors to explore the location and organization of the spinal center for erection.

The systematic knowledge of the neural anatomy of erection was generally accumulated as follows. The spinal nuclei for control of erection was found to be located in the inter-diolateral gray matter at the $S_{1-3}$ and $T_{12}$-$L_3$ level in a dog which is equivalent to the $S_{2-4}$ and $T_{10}$-$L_2$ in the human male. It was further found that from these sacral nuclei, axons issue ventrally and join the axons of the nuclei for the bladder and rectum to form the sacrovisceral efferent fibers. Such fibers emerge from the anterior root of $S_{2-4}$, join the sympathetic fibers to form the pelvic plexus, which then branches out to innervate bladder, rectum and penis.

The fibers innervating the penis (cavernous nerves) travel along the posterial lateral aspect of the seminal vesicle and prostate, then accompany the membranous urethra through the genitourinary diaphragm. Such nerves were further found to be located on the lateral aspect of the membranous urethra and gradually ascend to the one and eleven o'clock positions in the proximal bulbous urethra. Some of the fibers penetrate the tunica albuginea of the corpus spongiosum, whereas others spread over to the trifurcation of the terminal and internal pudendal artery and innervate the dorsal, deep and urethral arteries. Shortly prior to the point whereat the two corpora cavernosa merge, the cavernous nerves penetrate the tunica albuginea of the corpora, along with the deep artery and cavernous vein. The terminal branches of these nerves spread out to innervate the helicine arteries and the erectile tissue within the corpora cavernosa.

It can be seen, due to the intimate relationship of the nervi erigentes to the rectum, prostate, and urethra, that these nerves could be easily damaged during various urologic and pelvic procedures. As described more fully hereinafter, the preferred location of electrode 11 was found to be on or around the portions of the cavernous nerves located posterolaterally to the prostate gland and between the apex of the prostatic capsule and the sacral nerves. This precise location was confirmed by electrical stimulation of dog and monkey specimens. During this phase of experimentation and study, it was recognized that the intimate relationship of the cavernous nerves to the distal prostate has been long overlooked. In particular, studies have shown that radical prostatectomy constitutes a neurogenic basis for impotence. Violation of the integrity of the prostatic capsule by either surgery or infection can easily affect the cavernous nerves and cause sexual disability.

Having now fully studied the neural anatomy of an erection of the adult male, and, in particular, having determined the precise location on the cavernous nerve which, when stimulated, will induce an erection, the inventors proceeded to investigate the hemodynamics and mechanism of penile erection. Such investigation included the use of monkey models, each having an electrode surgically around each of its two cavernous nerves for purposes of inducing controlled erection. A monkey proved an ideal experimental model since its anatomy closely approaches that of a male human and the erection processes are substantially similar to each other.

These latter studies included selected data on arterial blood flow, corporeal pressure, blood gases, venous flow, and radiography. These studies indicated that tumescence of the corpora cavernosa was found to be the direct result of active relaxation of the sineusoidal spaces, active arteriolar dilation, and active venous constriction. At full erection, adequate but reduced blood flow occurred into and out of the corpora cavernosa for metabolic exchange. The above studies thus led to the following clinical implications and conclusions: (1) identification and isolation of the cavernous nerves can preserve potency in patients undergoing radical pelvic operations; (2) percutaneous stimulation of the cavernous nerves will aid in differentiating psychogenic impotency from organic impotency; and (3) the feasibility of the method of this invention for stimulating penile erection was proven.

Specific information on the above clinical experimentation and development work can be found in the publications "Neuroanatomy of Penile Erection: Its Relevance to Laterogenic Impotence" by Tom F. Lue, et al. appearing in the February, 1984 issue of *Journal of Urology*, Volume 131, pages 273-279 (First Prize, Joseph McCarthy Essay Competition, Western Section, American Urological Association, 1983) and "Hemodynamics of Penile Erection in the Monkey" by Tom F. Lue, et al. appearing in the December, 1983 issue of *Journel of Urology*, Volume 130, pages 1237-1241 (First Prize, Laboratory Research, American Urological Association, 1983).

Open Surgical Method (FIG. 1)

FIG. 1 illustrates the anatomy of the pelvic plexus of a human male, having a pair of electrodes 11 (one shown) of pacemaker system 10 surgically implanted therein, along with subcutaneous receiver 12. It should be understood that illustrated electrode 11 is implanted on each of a pair of the patient's cavernous nerves (FIG. 3).

The patient is first anaesthetized by use of an anaesthetic that will not affect his erection response. For example, it has been found that a combination of Fentanyl, oxygen, and nitrous oxide in proper amounts will not affect intraoperative stimulation and a responsive erection. After satisfactory anaesthesia, an incision is made on the lower abdomen to permit the surgeon to enter the extraperitoneal retropubic space. The lateral bladder wall, rectal wall, and the prostate, along with the pelvic plexus, are then exposed.

Electrical stimulation with a bipolar probe is then used to stimulate different bundles of the pelvic plexus. A Grass nerve stimulator 18 (FIG. 2) is then used to deliver a DC square wave for stimulation. Stimulation of the cavernous nerves are indicated by elongation, engorgement an pulsation of the penis. In one application, the Grass nerve stimulator constituted Model No. S-44, manufactured by Grass Medical Instruments of Quincy, Mass. After the cavernous nerves are identified, an electrode 11 is implanted around the identified bundle of cavernous nerves.

In one application, such electrode constituted a bipolar cuff electrode having an inside diameter approximating 3-5 mm. and provided with 1 mm. by 2 mm. platinum contacts having a 3 mm. separation placed opposite each other about the periphery of the Silastic cuff. This electrode is manufactured by Avery Laboratories, Inc. under Model No. 390. Extreme care was taken to protect such nerves from inadvertent damage. The adjacent soft tissue and preferably some accompanying blood vessels are included in the encapsulated bundle of the nerves for protection purposes.

Each electrode 11 is then suitably connected by leads 13, preferably Silastic coated multi-stranded stainless steel wires, to receiver 12 which is implanted subcutaneously in the lower abdomen region of the patient. Several stitches are used to secured the wire leads to the lateral abdominal wall. Each electrode is preferably implanted in place on portions of the cavernous nerve located between the sacral nerves and the apex of the prostate, depending, of course, on which portions or bundles of the cavernous nerves provide the best erection response for a particular patient. Each cuff electrode is anchored in place with a pair of stitches of fine sutures with wire leads 13 also being fixed with the same type of sutures to the lateral abdominal wall.

In one application, receiver 12 constituted an implantable Silastic coated unit containing an antenna coil adapted to receive "rf" pulses transmitted from an external transmitter 14, connected to an antenna ring 15 by a cable 16. The transmitted pulses are detected by the receiver, converted to the electrical stimulus pulses and transmitted to electrodes 11 by connected leads 13. This type of receiver is also manufactured by Avery Laboratories, Inc. under Model No. I-110 (bipolar). The transmitter constitutes a device which is battery-powered (9-volt) with a pulse generating circuit that produces pulses to turn the radio frequency (rf) carrier on and off (amplitude modulated) and delivers the pulse signal to antenna ring 15. The transmitter and antenna may also be of the type manufactured by Avery Laboratories, Inc. under Model No. S-218-1 and Model No. 9001A, respectively. The characteristics of the transmitter's stimuli are as follows:

amplitude—up to 14 volts,
load—1,000 ohm,
pulse width—50 to 200 microseconds,
pulse frequency—in the range of from 2-200 PPS.

Figure 4:
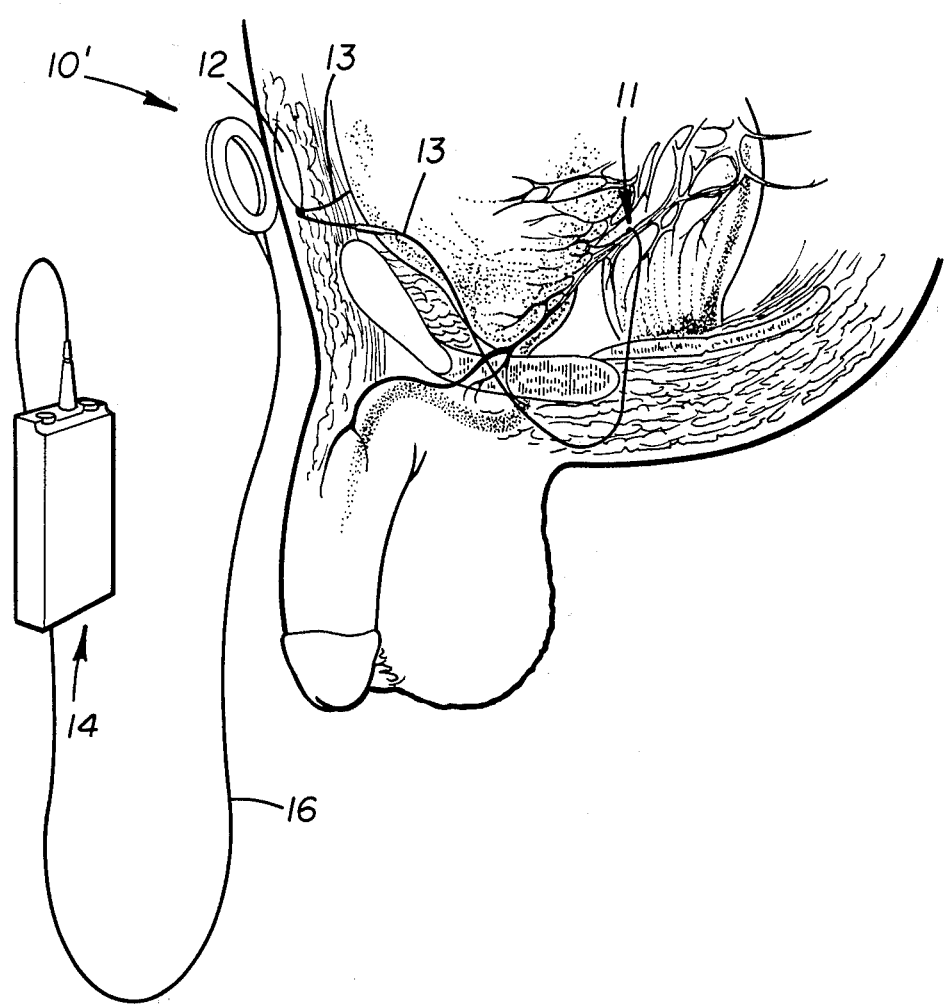
FIG. 4 is a view similar to FIG. 1, but illustrates final implantation of one of each electrode by use of the spinal needle, a subcutaneous receiver connected thereto, and an external transmitter.

Percutaneous Method (FIGS. 2–4)

FIGS. 2–4 illustrate an alternate pacemaker system 10' and a percutaneous method of implanting an electrode 11 on cavernous nerves C. With the patient in lithotomy position, and after the perineum has been shaved and prepped with antiseptic solution, an 18-gauge insulated spinal needle (12 cm. in length) is inserted per perineum towards the posterolateral aspect of the prostate anterior to the rectum. Electro-stimulation is then delivered to the tip of the spinal needle by above-mentioned Grass nerve stimulator 18 (FIG. 2).

When the needle engages the cavernous nerve for stimulation purposes, the penis will increase in length and diameter until full erection is reached. After verification of the appropriate depth and location of the critical nerve portions with the electro-stimulation, the obturator of the spinal needle is removed and wire electrode 11 is inserted through the needle to its final location on the cavernous nerve. As shown in FIG. 2, electrode 11 in this application constitutes a terminal end of wire lead 13.

Electro-stimulation is again delivered through wire 13 to each cavernous nerve to confirm the proper placement of the electrode, i.e., Grass nerve stimulator 18 is disconnected from needle 17 proper and reconnected to wire 13 for this purpose. The spinal needle is then removed and a subcutaneous tunnel is made to direct wire 13 to the lower abdomen for connection to subcutaneous receiver 12 (FIG. 4). Wite lead is then fixed in place using fixation sleeves which can be sutured to the fascia. Thereafter, external transmitter 14 and its ring antenna 15 can be utilized to transmit the radio frequency pulses to receiver 12, for purposes described above.

We claim:

1. A method for stimulating penile erection in a human male comprising the steps of
   identifying the anatomical location of at least one cavernous nerve of a penis,
   implanting electrode means at least closely adjacent to said cavernous nerve and intermediate the sacral nerves and the apex of the prostate,
   implanting a subcutaneous receiver on said human male,
   electrically connecting said electrode means to said receiver, and
   electrically energizing said receiver to transmit electrical energy to said electrode means and to said cavernous nerve.

2. The method of claim 1 wherein said implanting step comprises incising said patient and placing said electrode means on said cavernous nerve.

3. The method of claim 2 wherein said implanting step further comprises positioning said electrode means in enveloping relationship around said cavernous nerve.

4. The method of claim 1 wherein said identifying and locating step includes percutaneously inserting a needle electrode in said human male to engage said needle electrode with said cavernous nerve and electrically energizing said needle electrode to neurostimulate said cavernous nerve.

5. The method of claim 4 wherein said implanting step comprises implanting said electrode means through said hollow needle to position an end of said electrode means on said cavernous nerve.

6. The method of claim 5 wherein said electrically connecting step comprises percutaneously connecting said electrode means to said receiver by incising the skin of said human male and implanting an electrical lead therein.

7. The method of claim 1 wherein said electrically energizing step comprises placing an antenna of an external transmitter adjacent to said receiver to electrically couple said antenna with said receiver to transmit electrical energy to said electrode means and to said cavernous nerve.

8. The method of claim 1 further comprising the step anaesthetizing said human male with an anaesthetic that does not affect erection response.

9. The method of claim 8 wherein said anaesthetizing step includes anaesthetizing said human male with a mixture of Fentenyl, oxygen and nitrous oxide.

* * * * *

UNITED STATES PATENT AND TRADEMARK OFFICE
CERTIFICATE OF CORRECTION

PATENT NO. : 4,585,005
DATED : April 29, 1986
INVENTOR(S) : Lue et al.

It is certified that error appears in the above-identified patent and that said Letters Patent is hereby corrected as shown below:

On the title page:

Inventor Tom P. Lue's name should be changed to --Tom F. Lue--.

Signed and Sealed this

Second Day of December, 1986

*Attest:*

DONALD J. QUIGG

*Attesting Officer*  *Commissioner of Patents and Trademarks*